United States Patent [19]

Bird

[11] Patent Number: 5,478,843
[45] Date of Patent: Dec. 26, 1995

[54] THIAZOLE DERIVATIVES

[75] Inventor: Thomas G. C. Bird, Witry-les-Reims, France

[73] Assignees: Zeneca Limited, London, England; Zeneca Pharma S.A., Cergy Cedex, France

[21] Appl. No.: 277,890

[22] Filed: Jul. 20, 1994

[30] Foreign Application Priority Data

Jul. 27, 1993 [EP] European Pat. Off. ............. 93401947

[51] Int. Cl.$^6$ ................. C07D 215/227; C07D 215/36; C07D 417/12; A61K 31/47
[52] U.S. Cl. .................. 514/312; 546/155; 546/157; 546/158
[58] Field of Search .................. 546/155, 157, 546/158; 514/312

[56] References Cited

U.S. PATENT DOCUMENTS

| | | | |
|---|---|---|---|
| 4,567,184 | 1/1986 | Musser et al. | 514/277 |
| 4,625,034 | 11/1986 | Neiss et al. | 546/152 |
| 4,631,287 | 12/1986 | Chakraborty et al. | 514/307 |
| 4,725,619 | 2/1988 | Chakraborty et al. | 514/442 |
| 4,728,668 | 3/1988 | Chakraborty et al. | 514/464 |
| 4,794,188 | 12/1988 | Musser et al. | 546/152 |
| 4,839,369 | 6/1989 | Youssefyeh et al. | 514/314 |
| 4,868,193 | 9/1989 | Lee | 514/314 |
| 4,874,769 | 10/1989 | Youssefyeh et al. | 514/314 |
| 5,008,274 | 4/1991 | Nishi et al. | 514/312 |
| 5,098,930 | 3/1992 | Edwards et al. | 514/459 |
| 5,134,148 | 7/1992 | Crawley et al. | 514/312 |
| 5,196,419 | 3/1993 | Crawley et al. | 514/241 |
| 5,217,969 | 6/1993 | Bruneau et al. | 514/230.5 |
| 5,217,978 | 6/1993 | Bird | 514/312 |
| 5,221,677 | 6/1993 | Crawley et al. | 514/309 |
| 5,234,950 | 8/1993 | Edwards et al. | 514/473 |
| 5,236,919 | 8/1993 | Crawley et al. | 514/349 |
| 5,302,594 | 4/1994 | Crawley et al. | 514/249 |
| 5,302,603 | 4/1994 | Crawley et al. | 514/336 |
| 5,321,025 | 6/1994 | Bruneau et al. | 514/224.2 |
| 5,332,757 | 7/1994 | Bird | 514/459 |
| 5,334,614 | 8/1994 | Edwards et al. | 514/459 |
| 5,359,063 | 10/1994 | Bird | 544/105 |
| 5,367,079 | 11/1994 | Bruneau et al. | 546/157 |

FOREIGN PATENT DOCUMENTS 0485111  5/1992  European Pat. Off. .
WO9417054  8/1994  WIPO .

*Primary Examiner*—C. Warren Ivy
*Assistant Examiner*—D. Margaret M. Mach
*Attorney, Agent, or Firm*—Cushman Darby & Cushman

[57] ABSTRACT

The invention concerns a thiazole derivative of the formula I

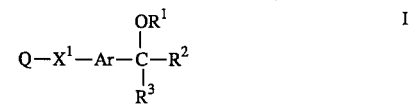

wherein Q is 2-oxo-1,2,3,4-tetrahydroquinolin-6-yl or 2-oxo-1,2-dihydroquinolin-6-yl which bears on the nitrogen atom at the 1-position a (1–4C)alkyl substituent;

$X^1$ is thio, sulphinyl or sulphonyl;

Ar is thiazolediyl;

$R^1$ is (1–4C)alkyl, (3–4C)alkenyl or (3–4C)alkynyl; and $R^2$ and $R^3$ together form a group of the formula —$A^2$—$X^2$—$A^3$— which together with the carbon atom to which $A^2$ and $A^3$ are attached define a ring having 5 or 6 ring atoms, wherein $A^2$ and $A^3$, which may be the same or different, each is (1–3C)alkylene and $X^2$ is oxy, and which ring may bear one or two (1–4C)alkyl substituents;

or a pharmaceutically-acceptable salt thereof;

processes for their preparation; pharmaceutical compositions containing them and their use as 5-lipoxygenase inhibitors.

7 Claims, No Drawings

THIAZOLE DERIVATIVES

This invention concerns thiazole derivatives and more particularly thiazole derivatives which are inhibitors of the enzyme 5-lipoxygenase (hereinafter referred to as 5-LO). The invention also concerns processes for the manufacture of said thiazole derivatives and novel pharmaceutical compositions containing them. Also included in the invention is the use of said thiazole derivatives in the treatment of various diseases such as inflammatory and/or allergic diseases in which the direct or indirect products of 5-LO catalysed oxidation of arachidonic acid are involved, and the production of new medicaments for such use.

As stated above the thiazole derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptidolipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various diseases, for example various inflammatory and allergic diseases such as inflammation of the joints (especially rheumatoid arthritis, osteoarthritis and gout), inflammation of the gastrointestinal tract (especially inflammatory bowel disease, ulcerative colitis and gastritis), skin diseases (especially psoriasis, eczema and dermatitis), ocular conditions (especially allergic conjunctivitis and uveitis) and respiratory disease (especially asthma, bronchitis and allergic rhinitis), for example in the production and development of various cardiovascular and cerebrovascular disorders such as myocardial infarction, the formation of atherosclerotic plaques, hypertension, platelet aggregation, angina, stroke, reperfusion injury, vascular injury including restenosis and peripheral vascular disease, for example in the formation of the conditions of shock or trauma such as can follow burn injuries, toxaemia or surgery, and for example various disorders of bone metabolism such as osteoporosis (including senile and postmenopausal osteoporosis), Paget's disease, bone metastases, hypercalcaemia, hyperparathyroidism, osteosclerosis, osteopetrosis and periodontitis, and the abnormal changes in bone metabolism which may accompany rheumatoid arthritis and osteoarthritis. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

It is disclosed in European Patent Applications Nos. 0385662 and 0420511 that certain heterocyclic derivatives possess inhibitory properties against 5-LO. In particular, European Patent Application No. 0462812 is also concerned with heterocyclene derivatives which possess inhibitory properties against 5-LO. The heterocyclene derivatives disclosed therein are of the formula

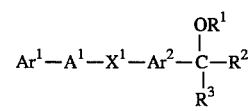

wherein $Ar^2$ is a 5-membered heterocyclene moiety containing one heteroatom selected from nitrogen, oxygen and sulphur such as pyrroldiyl, furandiyl and thiophenediyl. Particular compounds disclosed therein include the thiophenediyl derivatives: 4-methoxy-4-[5-(1-methyl-2-oxo-1,2,3,4-tetrahydroquinolin-6-ylthio)thien-2-yl] tetrahydropyran (Example 7 therein); and (2S,4R)-4-methoxy-2-methyl-4-[5 -(1-methyl-2-thioxo-1,2,3,4-tetrahydroquinolin-6-ylthio)thien-2-yl]tetrahydropyran (Example 12 therein).

There is no disclosure in European Patent Application No. 0462812 of compounds wherein $Ar^2$ is a 5-membered heterocyclene moiety containing two heteroatoms selected from nitrogen, oxygen and sulphur. In particular there is no disclosure of a compound wherein $Ar^2$ is a thiazolediyl group.

It has been found that certain compounds disclosed in European Patent Application No. 0462812 possess the undesirable property of auto-induction i.e. the repeated dosing of such a compound to a warm-blooded animal results in an increase in the efficiency with which the animal's hepatic enzymes metabolise the compound. The result is a decrease on repeat dosing of the quantity of the compound present in the animal's blood stream as shown, for example, by a decrease in the maximum concentration achieved (C max) or, for example, a decrease in the exposure of the animal to the compound as measured by the area under the curve (AUC) of a plot of the concentration of the compound in the blood stream versus time after dosing. The compound 4-methoxy-4-[5-(1-methyl-2-oxo-1,2,3,4-tetrahydroquinolin-6-ylthio)thien- 2-yl]tetrahydropyran possesses the undesirable property of auto-induction.

It has also been found that certain compounds disclosed in European Patent Application No. 0462812 are non-crystalline, for example they are formed in an oily or gummy state or they are isolated as foams. Such non-crystalline compounds are undesirable when consideration is given toward the preparation, purification, analysis, handling and formulation of larger quantities of the compounds. The compound (2S,4R)-4-methoxy-2-methyl-4-[5-(1-methyl-2-thioxo-1,2, 3,4 -tetrahydroquinolin-6-ylthio)thien-2-yl]tetrahydropyran possesses the undesirable property of being a viscous oil.

We have now discovered that certain thiazole derivatives are preferred inhibitors of the enzyme 5-LO and thus of leukotriene biosyntheses. Thus such compounds are of value as therapeutic agents in the treatment of, for example, allergic conditions, psoriasis, asthma, cardiovascular and cerebrovascular disorders, inflammatory and arthritic conditions, and/or disorders of bone metabolism, mediated alone or in part by one or more leukotrienes.

According to the invention there is provided a thiazole derivative of the formula I

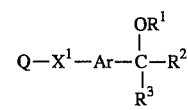

wherein Q is 2-oxo-1,2,3,4-tetrahydroquinolin-6-yl or 2-oxo-1,2-dihydroquinolin-6-yl which bears on the nitrogen atom at the 1-position a (1–4C)alkyl substituent;

$X^1$ is thio, sulphinyl or sulphonyl;

Ar is thiazolediyl;

$R^1$ is (1–4C)alkyl, (3–4C)alkenyl or (3–4C)alkynyl; and $R^2$ and $R^3$ together form a group of the formula —$A^2$—$X^2$—$A^3$— which together with the carbon atom to which $A^2$ and $A^3$ are attached define a ring having 5 or 6 ring atoms, wherein $A^2$ and $A^3$, which may be the same or different, each is (1–3C)alkylene and $X^2$ is oxy, and which ring may bear one or two (1–4C)alkyl substituents;

or a pharmaceutically-acceptable salt thereof.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is further to be understood that, insofar as certain of the compounds of formula I defined above may exist in optically active or racemic forms by virtue of one or more asymmetric carbon atoms, the invention includes in its definition any such optically active or racemic form which possesses the property of inhibiting 5-LO. The synthesis of optically active forms may be carried out by standard techniques of organic chemistry well known in the art, for example by synthesis from optically active starting materials or by resolution of a racemic form.

Suitable values for the generic terms referred to above include those set out below.

A suitable value for the (1–4C)alkyl substituent which is present on Q is, for example, methyl, ethyl or propyl.

A suitable value for Ar when it is thiazolediyl is, for example, 2,4-thiazolediyl or 2,5-thiazolediyl.

A suitable value for $R^1$ when it is (1–4C)alkyl is, for example, methyl, ethyl or propyl; when it is (3–4C)alkenyl is, for example, allyl; and when it is (3–4C)alkynyl is, for example, 2-propynyl.

When $R^2$ and $R^3$ together form a group of the formula —$A^2$—$X^2$—$A^3$— which together with the carbon atom to which $A^2$ and $A^3$ are attached define a ring having 5 or 6 ring atoms then a suitable value for $A^2$ or $A^3$, which may be the same or different when each is (1–3C)alkylene is, for example, methylene, ethylene or trimethylene. Suitable values for the (1–4C)alkyl substituents which may be present on said 5- or 6-membered ring include, for example, methyl and ethyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular compounds of the invention include, for example, thiazole derivatives of the formula I, or pharmaceutically-acceptable salts thereof, wherein the variable groups Q, $X^1$, Ar, $R^1$, $R^2$ and $R^3$ have the values disclosed hereinbefore or hereinafter in this section concerning particular compounds of the invention:

(a) Q is 1-methyl-2-oxo-1,2,3,4-tetrahydroquinolin-6-yl;

(b) $X^1$ is thio or sulphonyl;

(c) Ar is 2,4-thiazolediyl (with the $X^1$ group in the 2-position);

(d) Ar is 2,5-thiazolediyl (with the $X^1$ group in the 2-position);

(e) Ar is 2,5-thiazolediyl (with the $X^1$ group in the 5-position);

(f) $R^1$ is methyl; or (g) $R^2$ and $R^3$ together form a group of the formula —$A^2$—$X^2$—$A^3$— which together with the carbon atom to which $A^2$ and $A^3$ are attached define a ring having 5 or 6 ring atoms, wherein $A^2$ is methylene or ethylene, $A^3$ is ethylene and $X^2$ is oxy, and which ring may bear a methyl substituent alpha to $X^2$.

A preferred compound of the invention comprises a thiazole derivative of the formula I wherein Q is 1-methyl-2-oxo-1,2,3,4-tetrahydroquinolin-6-yl;

$X^1$ is thio or sulphonyl;

Ar is 2,5-thiazolediyl (with the $X^1$ group in the 2-position);

$R^1$ is methyl; and $R^2$ and $R^3$ together form a group of the formula —$A^2$—$X^2$—$A^3$— which together with the carbon atom to which $A^2$ and $A^3$ are attached define a ring having 6 ring atoms, wherein each of $A^2$ and $A^3$ is ethylene and $X^2$ is oxy, and which ring may bear a methyl substituent alpha to $X^2$;

or a pharmaceutically-acceptable salt thereof.

A further preferred compound of the invention comprises a thiazole derivative of the formula I wherein Q is 1-methyl-2-oxo-1,2,3,4-tetrahydroquinolin-6-yl, $X^1$ is thio or sulphonyl;

Ar is 2,5-thiazolediyl (with the $X^1$ group in the 2-position);

$R^1$ is methyl; and $R^2$ and $R^3$ together form a group of the formula —$CH_2CH_2OCH(CH_3)CH_2$—;

or a pharmaceutically-acceptable salt thereof.

A specific preferred compound of the invention is the following compound of the formula I:

(2S,4R)-4-methoxy-2-methyl-4-[2-(1-methyl-2-oxo-1,2,3,4-tetrahydroquinolin- 6-ylthio)thiazol-5-yl]tetrahydropyran.

In a further aspect of the invention we have now discovered that certain compounds of the invention lack to a substantial degree the undesirable property of auto-induction. Thus such compounds are of particular value in the treatment of various inflammatory and/or allergic diseases in warm-blooded animals as they lack the disadvantages which may arise as a result of auto-induction. Thus, for example, the assessment of pharmacological and toxicological data is made more complex if the test compound has been shown to possess a significant degree of auto-induction. In addition auto-induction may foreshadow the general induction of enzymes which could have disadvantageous effects such as a detrimental increase in the rate of metabolism of any co-administered drugs.

In another aspect of the invention we have discovered that certain compounds of the invention are crystalline. Thus such compounds are of value when their preparation on a larger scale is required. The purification, analysis and handling of a material is facilitated if it is formed in the crystalline state. It is known, for example, that the removal of solvent residues from non-crystalline, oily materials is problematical. In addition the preparation of a pharmaceutical composition comprising a crystalline material is a conventional procedure. The composition may, for example, be in a form suitable for oral use such as a tablet or capsule; or, for example, in a form suitable for administration by inhalation, for example as a finely divided powder or a microcrystalline form. Such options for the formulation of the material are precluded should it be formed in an oily state.

A compound of the invention comprising a thiazole derivative of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, Q, $X^1$, Ar, $R^1$, $R^2$ and $R^3$ have any of the meanings defined hereinbefore.

(a) The coupling, conveniently in the presence of a suitable base, of a compound of the formula Q—$X^1$—H with a compound of the formula II

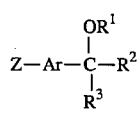

wherein Z is a displaceable group.

A suitable displaceable group Z is, for example, a halogeno or sulphonyloxy group, for example a fluoro, chloro, bromo, iodo, methane-sulphonyloxy or toluene-4-sulphonyloxy group.

A suitable base for the coupling reaction is, for example, an alkali or alkaline earth metal carbonate, (1–4C)alkoxide, hydroxide or hydride, for example sodium carbonate, potassium carbonate, sodium ethoxide, potassium butoxide, lithium hydroxide, sodium hydroxide, potassium hydroxide, sodium hydride or potassium hydride, or an organometallic base such as (1–4C)alkyl-lithium, for example n-butyl-lithium. The coupling reaction is conveniently performed in a suitable inert solvent or diluent, for example N,N-dimethylformamide, N,N-dimethylacetamide, N-methylpyrrolidin-2-one, dimethylsulphoxide, acetone, 1,2-dimethoxyethane or tetrahydrofuran, and at a temperature in the range, for example, 10° to 150° C., conveniently at or near 100° C.

Conveniently the reaction may be performed in the presence of a suitable catalyst, for example a metallic catalyst, for example palladium(0) or copper(I) such as tetrakis(triphenylphosphine)palladium, cuprous chloride or cuprous bromide.

The starting materials of the formula Q—$X^1$—H and of the formula II may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

(b) The coupling, conveniently in the presence of a suitable base as defined hereinbefore, of a compound of the formula Q—Z, wherein Z is a displaceable group as defined hereinbefore, with a compound of the formula III

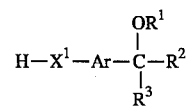

The coupling reaction is conveniently performed in a suitable inert solvent as defined hereinbefore and at a temperature in the range, for example, 10° to 150° C., conveniently at or near 100° C. The reaction may conveniently be performed in the presence of a suitable catalyst as defined hereinbefore.

The starting materials of the formula Q—Z and of the formula III may be obtained by standard procedures of organic chemistry. Alternatively necessary starting materials are obtainable by analogous procedures to those illustrated which are within the ordinary skill of an organic chemist. The disclosure of European Patent Application No. 0420511 is particularly relevant to the preparation of suitable starting materials.

(c) The coupling of a compound of the formula Q—$X^1$—Z, wherein Z is a displaceable group as defined hereinbefore or, when $X^1$ is a thio group, Z may be a group of the formula Q—$X^1$—, with an organometallic reagent of the formula IV

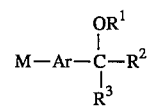

wherein M is an alkali metal or alkaline earth metal such as lithium or calcium or M represents the magnesium halide portion of a conventional Grignard reagent.

The coupling reaction is conveniently performed in a suitable inert solvent or diluent as defined hereinbefore and at a temperature in the range, for example, −80° to +50° C., conveniently in the range −80° C. to ambient temperature.

The preparation of the starting materials of the formula Q—$X^1$—Z and of the formula IV may be obtained by standard procedures of organic chemistry. Alternatively necessary starting materials are obtainable by analogous procedures to those illustrated which are within the ordinary skill of an organic chemist. The disclosure of the European Patent Applications set out hereinbefore are particularly relevant to the preparation of suitable starting materials.

(d) The alkylation, conveniently in the presence of a suitable base as defined hereinbefore, of a compound of the formula V

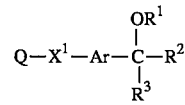

with a compound of the formula $R^1$—Z, wherein Z is a displaceable group as defined hereinbefore.

The alkylation reaction is conveniently performed in a suitable inert solvent or diluent as defined hereinbefore and at a temperature in the range, for example, −20° to +70° C., conveniently at or near ambient temperature.

The preparation of the starting materials of the formula V may be obtained by standard procedures of organic chemistry. Alternatively necessary starting materials are obtainable by analogous procedures to those illustrated in the European Patent Applications set out hereinbefore.

(e) For the production of those compounds of the formula I wherein Q bears an alkyl substituent on an available nitrogen atom, the alkylation of a compound of the formula I wherein Q bears a hydrogen atom on said available nitrogen atom.

A suitable alkylating agent is, for example, any agent known in the art for the alkylation of an available nitrogen atom, for example an alkyl halide, for example a (1–4C)alkyl chloride, bromide or iodide, in the presence of a suitable base as defined hereinbefore. The alkylation reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, 10° to 150° C., conveniently at or near ambient temperature.

(f) For the production of those compounds of the formula I wherein $X^1$ is a sulphinyl or sulphonyl group, the oxidation of a compound of the formula I wherein $X^1$ is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

As stated previously, the compounds of the formula I are inhibitors of the enzyme 5-LO. The effects of this inhibition may be demonstrated using one or more of the standard procedures set out below:

a) An in vitro assay system involving incubating a test compound with heparinised human blood, prior to challenge with the calcium ionophore A23187 and then indirectly measuring the inhibitory effects on 5-LO by assaying the amount of $LTB_4$ using specific radioimmunoassays described by Carey and Forder (F. Carey and R. A. Forder, *Prostaglandins, Leukotrienes Med.*, 1986, 22, 57; *Prostaglandins*, 1984, 28, 666; *Brit. J. Pharmacol.* 1985, 84, 34P) which involve the use of a protein-$LTB_4$ conjugate produced using the procedure of Young et alia (*Prostaglandins*, 1983, 26(4), 605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TxB_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

b) An ex vivo assay system, which is a variation of test a) above, involving administration to a group of rats of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

c) An in vivo system involving measuring the effects of a test compound administered orally to a group of male rats against the liberation of $LTB_4$ induced by zymosan within an air pouch generated within the subcutaneous tissue of the back of each rat. The rats are anaesthetised and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in at least one of the above tests a)–c):

Test a): $IC_{50}$ ($LTB_4$) in the range, for example, 0.01–40 μM $IC_{50}$ ($TxB_2$) in the range, for example, 40–200 μM;

Test b): oral $ED_{50}(LTB_4)$ in the range, for example, 0.1–100 mg/kg;

Test c): oral $ED_{50}(LTB_4)$ in the range, for example, 0.1–100 mg/kg.

No overt toxicity or other untoward effects are present in tests b) and/or c) when compounds of the formula I are administered at several multiples of their minimum inhibitory dose or concentration.

Thus, by way of example, the compound (2S,4R)-4-methoxy-2-methyl-4-[2-(1-methyl-2-oxo-1,2,3,4-tetrahydroquinolin- 6-ylthio)thiazol-5-yl]tetrahydropyran has an $IC_{50}$ of 0.06 μM against $LTB_4$ in test a), and an $IC_{50}$ of approximately 0.2 mg/kg against $LTB_4$ in test c).

These compounds are examples of compounds of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a thiazole derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a thiazole derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a thiazole derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a compound of the formula I will naturally vary according to the nature and severity of the conditions, the age and sex of the animal or patient and the route of administration, according to well known principles of medicine. As mentioned above, compounds of the formula I are useful in treating those diseases such as allergic and inflammatory conditions and disorders of bone metabolism which are due alone or in part to the effects of the metabolites of arachidonic acid arising by the linear (5-LO catalysed) pathway and in particular the leukotrienes, the production of which is mediated by 5-LO. As previously mentioned, such conditions include, for example, various inflammatory and allergic diseases such as inflammation of the joints (especially rheumatoid arthritis, osteoarthritis and gout), inflammation of the gastrointestinal tract (especially inflammatory bowel disease, ulcerative colitis and gastritis), skin diseases (especially psoriasis, eczema and dermatitis), ocular conditions (especially allergic conjunctivitis and uveitis) and respiratory disease (especially asthma, bronchitis and allergic rhinitis), for example in the production and development of various cardiovascular and cerebrovascular disorders such as myocardial infarction, the formation of atherosclerotic plaques, hypertension, platelet aggregation, angina, stroke, reperfusion injury, vascular injury including restenosis and peripheral vascular disease, for example in the formation of the conditions of shock or trauma such as can follow burn injuries, toxaemia or surgery, and for example various disorders of bone metabolism such as osteoporosis (including senile and postmenopausal osteoporosis), Paget's disease, bone metastases, hypercalcaemia, hyperparathyroidism, osteosclerosis, osteopetrosis and periodontitis, and the abnormal changes in bone metabolism which may accompany rheumatoid arthritis and osteoarthritis.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a thiazole derivative of the formula I, or a pharmaceutically-acceptable salt thereof as defined hereinbefore, in conjunction or admixture with a cyclooxygenase inhibitory non-steroidal anti-inflammatory agent (such as those mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) the end-products of the formula I have satisfactory microanalyses and their structures were confirmed by nuclear magnetic resonance (NMR) and mass spectral techniques; unless otherwise stated, $CDCl_3$ solutions of the end-products of the formula I were used for the determination of NMR spectral data, chemical shift values were measured on the delta scale; the following abbreviations have been used: s, singlet; d, doublet; t, triplet; m, multiplet;

(vi) intermediates were not generally fully characterised and purity was assessed by thin layer chromatographic, infra-red (IR) or NMR analysis;

(vii) melting points are uncorrected and were determined using a Mettier SP62 automatic melting point apparatus or an oil-bath apparatus; melting points for the end-products of the formula I were determined after crystallisation from a conventional organic solvent such as ethanol, methanol, acetone, ether or hexane, alone or in admixture; and (viii) the following abbreviation has been used:

NMP N-methylpyrrolidin-2-one;

THF tetrahydrofuran;

DMF N,N-dimethylformamide.

EXAMPLE 1

6-Mercapto-1-methyl-1,2,3,4-tetrahydroquinolin-2-one (0.166 g) was added to a mixture of 4-(2-chlorothiazol-5-yl)-4-methoxytetrahydropyran (0.2 g), potassium carbonate (0.13 g) and NMP (2 ml). The mixture was stirred and heated to 100° C. for 3 hours. The mixture was cooled to ambient temperature and partitioned between ethyl acetate and water. The organic phase was washed with brine, dried ($MgSO_4$) and evaporated. The residue was purified by column chromatography using a 1:1 mixture of petroleum ether (b.p. 40°–60° C.) and ethyl acetate as eluent. There was thus obtained 4-methoxy-4-[2-(1-methyl-2-oxo- 1,2,3,4-tetrahydroquinolin-6-ylthio)thiazol-5-yl]tetrahydropyran (0.25 g), m.p. 114°–115° C. (recrystallised from ethanol);

NMR Spectrum 1.97–2.01 (m, 4H), 2.69 (m, 2H), 2.94 (m, 2H), 3.05 (s, 3H), 3.38 (s, 3H), 3.7–3.8 (m, 4H), 7.02–7.04 (d, 1H), 7.45 (s, 1H), 7.46–7.47 (d, 1H), 7.55–7.58 (m, 1H).

The 6-mercapto-1-methyl-1,2,3,4-tetrahydroquinolin-2-one used as a starting material was obtained as follows:

A mixture of concentrated hydrochloric acid (5 drops) and water (50 ml) was added to a stirred mixture of di-(1-methyl-2-oxo-1,2,3,4-tetrahydroquinolin-6-yl) disulphide (European Patent Application No. 0462812, Example 7 thereof; 38.4 g), triphenylphosphine (29 g) and 1,4-dioxan (300 ml). The mixture was stirred at ambient temperature for 30 minutes. The mixture was concentrated by evaporation to reduce the volume by approximately one half. The residue was partitioned between ethyl acetate and 0.5N aqueous sodium hydroxide solution. The aqueous phase was washed with diethyl ether and then acidified to pH2 by the addition of dilute aqueous hydrochloric acid. The acidic mixture was extracted with ethyl acetate. The organic phase was dried ($MgSO_4$) and evaporated. The residual oil was dissolved in diethyl ether and hexane was added. There was thus obtained 6-mercapto-1-methyl-1,2,3,4-tetrahydroquinolin-2-one as a solid (35.5 g, 92%) which was used without further purification.

The 4-(2-chlorothiazol-5-yl)-4-methoxytetrahydropyran used as a starting material was obtained as follows:

A saturated aqueous solution of sodium nitrite (6.9 g) was added dropwise to a stirred solution of 2-aminothiazole (10 g) in concentrated hydrochloric acid (50 ml) which had been cooled to 0° C. The mixture was stirred at 0° C. for 75 minutes. Cuprous chloride (9.9 g) was added portionwise, the reaction temperature being maintained at 0° C., and the mixture was stirred for 2.5 hours. The mixture was neutralised by the addition of 10N aqueous sodium hydroxide solution. The mixture was partitioned between diethyl ether and water. The organic phase was washed with brine, dried ($MgSO_4$) and evaporated. The residue was purified by distillation. There was thus obtained 2-chlorothiazole (3.95 g, b.p. 68° C. at 68 mm of mercury).

A solution of 2-chlorothiazole (0.5 g) in diethyl ether (4 ml) and n-butyl-lithium (2.5M in hexane, 1.8 ml) were added simultaneously to diethyl ether (5 ml) which had been cooled to −78° C. The mixture was stirred and allowed to warm to −20° C. A solution of tetrahydropyran-4-one (0.42 g) in diethyl ether (5 ml) was added dropwise. The mixture was stirred for 1 hour and allowed to warm to 0° C. and then allowed to warm to ambient temperature. The mixture was partitioned between diethyl ether and a saturated aqueous ammonium chloride solution. The organic phase was washed with brine, dried ($MgSO_4$) and evaporated. The residue was purified by column chromatography using a 1:1 mixture of petroleum ether (b.p. 40°–60° C.) and ethyl acetate as eluent. There was thus obtained 4-(2-chlorothiazol-5-yl)-4-hydroxytetrahydropyran (0.25 g, 27%), m.p. 94° C.

Sodium hydride [0.045 g (obtained after removal of the mineral oil dispersant)] was added to a solution of 4-(2-chlorothiazol-5-yl)-4-hydroxytetrahydropyran (0.2 g) in THF (1.5 ml) and the mixture was stirred at ambient temperature for 1 hour. Methyl iodide (0.17 ml) was added and the mixture was stirred at ambient temperature for 12 hours. The mixture was evaporated and the residue was partitioned between diethyl ether and brine. The organic phase was dried ($MgSO_4$) and evaporated. The residue was purified by column chromatography using a 1:1 mixture of petroleum ether (b.p. 40°–60° C.) and ethyl acetate as eluent. There was thus obtained 4-(2-chlorothiazol-5-yl)-4-methoxytetrahydropyran (0.2 g, 94%) as an oil.

EXAMPLE 2

3-Chloroperoxybenzoic acid (0.141 g) was added to a stirred solution of 4-methoxy-4-[2-(1-methyl-2-oxo-1,2,3,4-tetrahydroquinolin-6-ylthio)thiazol- 5-yl]tetrahydropyran (0.08 g) in methylene chloride (1.5 ml). The mixture was stirred at ambient temperature for 5 hours. A saturated aqueous sodium bicarbonate solution was added and the mixture was extracted with ethyl acetate. The organic phase was washed with brine, dried ($MgSO_4$) and evaporated. There was thus obtained 4-methoxy-4-[2-(1-methyl-2-oxo-1,2,3,4-tetrahydroquinolin-6 -ylsulphonyl)thiazol-5-yl]tetrahydropyran (0.071 g), m.p. 163°–164° C. (recrystallised from ethanol);

NMR Spectrum 2.03–2.05 (m, 4H), 2.70 (m, 2H), 3.0 (m, 2H), 3.1 (s, 3H), 3.38 (s, 3H), 3.78–3.81 (m, 4H), 7.12 (d, 1H), 7.73 (s, 1H), 7.9 (m, 1H), 7.98–8.01 (m, 1H).

EXAMPLE 3

Using an analogous procedure to that described in Example 1, 6-mercapto-1-methyl-1,2,3,4-tetrahydroquinolin-2-one was reacted with (2S,4R)-4-(2-chlorothiazol-5-yl)-4-methoxy-2-methyltetrahydropyran to give (2S,4R)-4-methoxy-2-methyl-4-[2-(1-methyl-2-oxo-1,2,3,4-tetrahydroquinolin- 6-ylthio)thiazol-5-yl]tetrahydropyran in 95Z yield as a foam;

NMR Spectrum 1.16–1.18 (d, 3H), 1.54–1.57 (m, 1H), 1.81–2.02 (m, 3H), 2.67–2.71 (m, 2H), 2.92–2.96 (m, 2H), 3.04 (s, 3H), 3.38 (s, 3H), 3.77–3.82 (m, 3H), 7.02–7.04 (d, 1H), 7.42 (s, 1H), 7.46 (m, 1H), 7.56 (m, 1H).

The (2S,4R)-4-(2-chlorothiazol-5-yl)-4-methoxy-2-methyltetrahydropyran used as a starting material was obtained as follows:

A solution of 2-chlorothiazole (0.5 g) in diethyl ether (4 ml) and n-butyl-lithium (2.5M in hexane, 1.8 ml) were added simultaneously during 10 minutes to diethyl ether (5 ml) which had been cooled to −78° C. The mixture was stirred for 3.5 hours and allowed to warm to −20° C. The mixture was recooled to −78° C. and a solution of (2S)-2-methyltetrahydropyran-4-one [European Patent Application No. 0385662 (Example 20 thereof); 0.43 g] in diethyl ether (4 ml) was added. The mixture was stirred and allowed to warm to −10° C. A 5% aqueous solution of ammonium chloride was added and the mixture was extracted with diethyl ether. The organic phase was washed with brine, dried (MgSO$_4$) and evaporated. The residue was purified by column chromatography using a 1:1 mixture of petroleum ether (b.p. 40°–60° C.) and ethyl acetate as eluent. There was thus obtained (2S,4R)-4-(2-chlorothiazol-5-yl)-4-hydroxy-2-methyltetrahydropyran (0.11 g, 13%) as an oil.

Sodium hydride (0.127 g, 5.27 mmol) was added to a solution of the 4-hydroxy-2-methyltetrahydropyran so obtained in THF (2.5 ml) and the mixture was stirred at ambient temperature for 1 hour. The mixture was cooled to 0° C. and methyl iodide (0.33 ml) was added. The mixture was stirred at ambient temperature for 2.5 hours. The mixture was evaporated and the residue was partitioned between diethyl ether and brine. The organic phase was dried (MgSO$_4$) and evaporated. The residue was purified by column chromatography using a 1:1 mixture of petroleum ether (b.p. 40°–60° C.) and ethyl acetate as eluent. There was thus obtained (2S,4R)-4-(2-chlorothiazol-5-yl)-4-methoxy-2-methyltetrahydropyran (0.268 g, 71%) as an oil which crystallised on standing.

EXAMPLE 4

Using an analogous procedure to that described in Example 2, (2S,4R)-4-methoxy-2-methyl-4-[2-(1-methyl-2-oxo-1,2,3,4-tetrahydroquinolin- 6-ylthio)thiazol-5-yl]tetrahydropyran was oxidised to give (2S,4R)-4-methoxy-2-methyl-4-[2-(1-methyl-2-oxo-1,2,3,4-tetrahydroquinolin-6-ylsulphonyl)thiazolo5-yl]tetrahydropyran in 98% yield as a foam;

NMR Spectrum 1.18–1.20 (d, 3H), 1.61–1.65 (m, 1H), 1.94–2.10 (m, 3H), 2.68–2.72 (m, 2H), 2.98–3.02 (m, 2H), 3.09 (s, 3H), 3.38 (s, 3H), 3.81–3.87 (m, 3H), 7.11–7.13 (d, 1H), 7.71 (s, 1H), 7.89–7.90 (m, 1H), 7.98–8.01 (m, 1H).

EXAMPLE 5

Potassium carbonate (15.5 g) was added to a solution of 6-mercapto-1-methyl-1,2,3,4-tetrahydroquinolin-2-one (19.7 g) in NMP (140 ml) and the mixture was stirred at ambient temperature for 10 minutes. (2S,4R)-4-(2-Chlorothiazol-5-yl)-4-methoxy-2-methyltetrahydropyran (25.2 g) was added and the mixture was stirred and heated to 100° C. for 2 hours. The mixture was cooled to ambient temperature and partitioned between diethyl ether and water. The organic phase was washed with water and with brine, dried (MgSO$_4$) and evaporated. The residue was triturated under diethyl ether to give a crystalline solid. There was thus obtained (2S,4R)-4-methoxy-2-methyl-4 -[2-(1-methyl-2-oxo-1,2,3,4-tetrahydroquinolin-6-ylthio)thiazol-5-yl]tetrahydropyran (37.5 g, 91%), m.p. 78°–79° C. (recrystallised from diethyl ether).

The (2S,4R)-4-(2-chlorothiazol-5-yl)-4-methoxy-2-methyltetrahydropyran used as starting material was obtained as follows:

n-Butyl-lithium (2.5M in hexane, 57.5 ml) was dropwise added during 30 minutes to a solution of di-isopropylamine (19.3 ml) in THF (180 ml) which had been cooled to −78° C. The mixture was stirred at −78° C. for 1 hour. The reaction vessel was shielded from light and 2-chlorothiazole (15.0 g) was added dropwise during 20 minutes, whilst keeping the temperature of the reaction mixture below −70° C. The mixture was stirred at −78° C. for 1.5 hours. (2S)-2-Methyltetrahydropyran-4-one (12.9 g) was added during 20 minutes. The mixture was stirred and allowed to warm briefly to −25° C. to obtain a homogeneous solution. The mixture was recooled to −70° C. and stirred at that temperature for 1 hour. A 5% aqueous solution of ammonium chloride was added and the mixture was extracted with diethyl ether. The organic solution was washed with brine, dried (MgSO$_4$) and evaporated. There was thus obtained a mixture (29.4 g) of (2S,4R)-4-(2-chlorothiazol-5-yl)-4-hydroxy-2-methyltetrahydropyran and the corresponding (2S, 4S)-isomer in a ratio of 1:4. The mixture so obtained was dissolved in diethyl ether (250 ml) and the solution was cooled to 0° C. A concentrated (25% v/v) aqueous solution of sulphuric acid was added and the mixture was stirred and allowed to warm to ambient temperature. The mixture was stirred at ambient temperature for 16 hours. The mixture was diluted with ethyl acetate (750 ml) and neutralised to pH3 by the addition of sodium bicarbonate. The organic solution was washed with brine, dried (MgSO$_4$) and evaporated to give a mixture (26 g) of (2S,4R)-4-(2-chlorothiazol-5-yl)-4-hydroxy-2-methyltetrahydropyran and the corresponding (2S,4S)-isomer in a ratio of 9:1. The material was purified by column chromatography using a 1:1 mixture of petroleum ether (b.p. 40°–60° C.) and ethyl acetate as eluent. There was thus obtained (2S,4R)-4-(2-chlorothiazol-5-yl)-4-hydroxy-2-methyltetrahydropyran (21 g, 79%).

Sodium hydride (60% dispersion in mineral oil, 14.5 g, 0.36 mol) was added portionwise during 15 minutes to a solution of (2S,4R)-4-(2-chlorothiazol-5-yl)-4-hydroxy-2-methyltetrahydropyran (42.15 g) in THF (150 ml) which had been cooled to 0° C. The mixture was stirred at 0° C. for 45 minutes. Methyl iodide (22.5 ml) was added dropwise and the mixture was stirred and allowed to warm to ambient temperature during 2 hours. The mixture was recooled to 0° C. and a solution of brine was added. The mixture was extracted with ethyl acetate. The organic solution was washed with brine, dried (MgSO$_4$) and evaporated. The residue was purified by column chromatography using a 7:3 mixture of petroleum ether (b.p. 40°–60° C.) and ethyl acetate as eluent. There was thus obtained (2S,4R)-4-(2-chlorothiazol-5 -yl)-4-methoxy-2-methyltetrahydropyran (40.9 g, 91%), m.p. 40°–42° C.

EXAMPLE 6

Using an analogous procedure to that described in Example 1 except that a catalytic amount (0.01 g) of potassium iodide was added, 6-mercapto-1-methyl-1,2,3,4-tetrahydroquinolin-2-one was reacted with 4-(2-chlorothiazol-5-yl)-4-methoxy-2,2-dimethyltetrahydropyran to give 4-methoxy-2,2-dimethyl-4-[2-(1-methyl-2-oxo-1,2,3,4-tetrahydroquinolin- 6-ylthio)thiazol-5-yl]tetrahydropyran in 80% yield as a foam;

NMR Spectrum 1.2 (s, 3H), 1.4 (s, 3H), 1.6–1.75 (m, 2H), 1.9–2.0 (m, 2H), 2.70 (m, 2H), 2.95 (m, 2H), 3.02 (s, 3H), 3.4 (s, 3H), 3.65 (m, 1H), 3.95 (m, 1H), 7.03 (m, 1H), 7.42 (s, 1H), 7.46 (m, 1H), 7.55 (m, 1H).

The 4-(2-chlorothiazol-5-yl)-4-methoxy-2,2-dimethyltetrahydropyran used as a starting material was obtained as follows:

A solution of 2-chlorothiazole (0.75 g) in diethyl ether (8 ml) and n-butyl-lithium (1.4M in hexane, 4.5 ml) were added simultaneously but separately to diethyl ether (8 ml) which had been cooled to −80° C. The mixture was stirred at −75° C. for 10 minutes and then allowed to warm to −30° C. The mixture was recooled to −80° C. and a solution of 2,2-dimethyltetrahydropyran-4-one (0.76 g) in diethyl ether (5 ml) was added. The mixture was stirred and allowed to warm to −30° C. The mixture was poured onto a mixture of ice and a saturated aqueous ammonium chloride solution. The organic solution was washed with brine, dried (MgSO$_4$) and evaporated. The residue was purified by column chromatography using a 10:3 mixture of hexane and ethyl acetate as eluent. There was thus obtained 4-(2-chlorothiazol-5-yl)-4-hydroxy-2,2-dimethyltetrahydropyran (0.67 g, 46Z) as an oil;

NMR Spectrum 1.2 (s, 3H), 1.45 (s, 3H), 1.8–2.15 (m, 4H}, 3.75 (m, 1H), 4.1 (m, 1H), 7.38 (s, 1H).

Using an analogous procedure to that described in the last paragraph of the portion of Example 3 which is concerned with the preparation of starting materials except that DMF was used as the reaction solvent in place of THF, the 4-hydroxy-2,2-dimethyltetrahydropyran so obtained was methylated to give 4-(2-chlorothiazol-5-yl)-4-methoxy-2,2-dimethyltetrahydropyran in 79% yield as an oil.

EXAMPLE 7

Sodium hydride (60% dispersion in mineral oil, 0.06 g) was added portionwise to a stirred solution of 4-hydroxy-2,6-dimethyl-4-[2-(1-methyl- 2-oxo-1,2,3,4-tetrahydroquinolin- 6-ylthio)thiazol-5-yl]tetrahydropyran (0.27 g) in DMF (2 ml) which had been cooled to 0° C. The mixture was stirred at 0° C. for 30 minutes. Methyl iodide (0.2 ml) was added. The mixture was allowed to warm to ambient temperature and was stirred for 16 hours. The mixture was partitioned between ethyl acetate and a saturated aqueous ammonium chloride solution. The organic solution was washed with brine, dried (MgSO$_4$) and evaporated. The residue was purified by column chromatography using increasingly polar mixtures of hexane and ethyl acetate as eluent. There was thus obtained 4-methoxy-2,6-dimethyl-4-[2-(1-methyl-2-oxo-1,2,3,4 -tetrahydroquinolin-6-ylthio-)thiazol-5-yl]tetrahydropyran (0.063 g) as a gum;

NMR Spectrum 1.15 (d, 3H), 1.4 (d, 3H), 1.65 (m, 2H), 1.9–2.1 (m, 2H), 2.70 (m, 2H), 2.95 (m, 2H), 3.05 (s, 3H), 3.37 (s, 3H), 4.1 (m, 2H), 7.03 (m, 1H), 7.40 (s, 1H), 7.47 (m, 1H), 7.55 (m, 1H).

The 4-hydroxy-2,6-dimethyl-4-[2-(1-methyl-2-oxo-1,2,3,4 -tetrahydroquinolin-6-ylthio)thiazol-5-yl]tetrahydropyran used as a starting material was obtained as follows:

The procedure described in the first paragraph of the portion of Example 6 which is concerned with the preparation of starting materials was repeated except that 2,6-dimethyltetrahydropyran-4-one was used in place of 2,2-dimethyltetrahydropyran-4-one. There was thus obtained 4-(2-chlorothiazol-5-yl)-4-hydroxy-2,6-dimethyltetrahydropyran in 77% yield.

NMR Spectrum 1.2 (s, 3H), 1.5 (s, 3H), 1.7–2.0 (m, 3H), 2.16 (m, 2H), 4.2 (m, 2H), 7.38 (s, 1H).

A mixture of 6-mercapto-1-methyl-1,2,3,4-tetrahydroquinolin-2-one (0.32 g), 4-(2-chlorothiazol-5-yl)-4-hydroxy-2,6-dimethyltetrahydropyran (0.3 g), potassium carbonate (0.33 g), potassium iodide (0.01 g) and DMF (3 ml) was stirred and heated to 100° C. for 4 hours. The mixture was cooled to ambient temperature and partitioned between ethyl acetate and a saturated aqueous ammonium chloride solution. The organic solution was washed with brine, dried (MgSO$_4$) and evaporated. The residue was purified by column chromatography using increasingly polar mixtures of hexane and ethyl acetate as eluent. There was thus obtained 4-hydroxy-2,6-dimethyl-4-[2-(1-methyl-2-oxo-1, 2,3,4 -tetrahydroquinolin-6-ylthio)thiazol-5-yl]tetrahydropyran (0.26 g, 53%) as a foam;

NMR Spectrum 1.2 (s, 3H), 1.5 (s, 3H), 1.7–1.9 (m, 3H), 2.15 (m, 1H), 2.66 (m, 1H), 2.95 (m, 2H), 3.39 (s, 3H), 4.18 (m, 2H), 7.0 (d, 1H), 7.5 (m, 2H), 7.55 (m, 1H).

EXAMPLE 8

Using an analogous procedure to that described in Example 1 except that triphenylphosphine (0.04 g) was added, 6-mercapto-1-methyl-1,2,3,4-tetrahydroquinolin-2-one (0.153 g) was reacted with (2S,4R)-4-(5-bromothiazol-2-yl)-4-methoxy-2-methyltetrahydropyran (0.23 g) to give (2S,4R)-4-methoxy-2-methyl-4-[5-(1 -methyl-2-oxo-1,2,3, 4-tetrahydroquinolin-6-ylthio)thiazol-2-yl]-tetrahydropyran in 72% yield as a foam;

NMR Spectrum 1.15–1.20 (d, 3H), 1.60 (m, 1H), 1.90–2.05 (m, 3H), 2.65–2.75 (m, 2H), 2.90–3.00 (m, 2H), 3.05 (s, 3H), 3.4 (s, 3H), 3.75–3.85 (m, 3H), 7.05 (d, 1H), 7.4 (s, 1H), 7.45 (m, 1H), 7.55 (m, 1H).

The (2S,4R)-4-(5-bromothiazol-2-yl)-4-methoxy-2-methyltetrahydropyran used as starting material was obtained as follows:

A solution of 2,5-dibromothiazole (2 g, *J. Chem. Soc., Perkin Trans.* I, 1992, 215–219) in diethyl ether (3 ml) was added dropwise to a solution of n-butyl-lithium (2.5M in hexane, 3.7 ml) in diethyl ether (80 ml) which has been cooled to −100° C. The mixture was stirred for 5 minutes and (2S)-2-methyltetrahydropyran-4-one (0.845 g) added, whilst maintaining the temperature of the reaction mixture at −100° C. The mixture was stirred for 45 minutes and quenched with a 5% aqueous solution of ammonium chloride. The mixture was extracted twice with diethyl ether, washed with brine, dried (MgSO$_4$), filtered and evaporated. The oil was purified by column chromatography using a 1:1 mixture of petroleum ether and ethyl acetate as eluent. There was thus obtained a mixture (1.177 g, 46%) of (2S,4S)- and (2S,4R)-4-(5-bromothiazol-2-yl)-4-hydroxy-2-methyltetrahydropyran as an oil.

The mixture so obtained (1 g) was dissolved in diethyl ether (15 ml) and the solution cooled to 0° C. A concentrated (30% v/v) aqueous solution of sulphuric acid (10 ml) was added and the mixture was stirred and allowed to warm to ambient temperature. The mixture was stirred at ambient temperature for 16 hours. The mixture was neutralised by the addition of sodium bicarbonate and extracted three times with diethyl ether, washed with brine, dried (MgSO$_4$), filtered and evaporated. The oil was purified by column chromatography using a 1:1 mixture of petroleum ether and ethyl acetate as eluent. There was thus obtained (2S,4R)-4-(5-bromothiazol-2-yl)-4-hydroxy-2-methyltetrahydropyran as a solid (0.707 g, 70%).

Sodium hydride (60% dispersion in mineral oil, 0.045 g, 0.0018 mol) was added to a solution of (2S,4R)-4-(5-bromothiazol-2-yl)-4-hydroxy-2-methyltetrahydropyran (0.25 g) in THF (2.5 ml) which had been cooled to 0° C. The mixture was stirred at 0° C. for 45 minutes. Methyl iodide (0.13 ml) was added dropwise and the mixture was stirred and allowed to warm to ambient temperature during 2 hours. A solution of brine was added and the organic solution extracted with ethyl acetate, dried (MgSO$_4$), filtered and evaporated. The oil was purified by column chromatography using a 1:2 mixture of petroleum ether and ethyl acetate as eluent. There was thus obtained (2S,4R)-4-(5-bromothiazol-2-yl)-4-methoxy-2-methyltetrahydropyran as an oil (0.233 g, 89%).

EXAMPLE 9

The following illustrate representative pharmaceutical dosage forms containing the compound of formula I, or a pharmaceutically-acceptable salt thereof (hereafter compound X), for therapeutic or prophylactic use in humans:

(a) Tablet I — mg/tablet

| | |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

(b) Tablet II — mg/tablet

| | |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

(c) Tablet III — mg/tablet

| | |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

(d) Capsule — mg/capsule

| | |
|---|---|
| Compound X | 10 |
| Lactose Ph.Eur | 488.5 |
| Magnesium stearate | 1.5 |

(e) Injection I — (50 mg/ml)

| | |
|---|---|
| Compound X | 5.0% w/v |
| 1 M Sodium hydroxide solution | 15.0% v/v |
| 0.1 M Hydrochloric acid (to adjust pH to 7.6) | |
| Polyethylene glycol 400 | 4.5% w/v |
| Water for injection to 100% | |

(f) Injection II — (10 mg/ml)

| | |
|---|---|
| Compound X | 1.0% w/v |
| Sodium phosphate BP | 3.6% w/v |
| 0.1 M Sodium hydroxide solution | 15.0% v/v |
| Water for injection to 100% | |

(g) Injection III — (1 mg/ml, buffered to pH6)

| | |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

(h) Aerosol I — mg/ml

| | |
|---|---|
| Compound X | 10.0 |
| Sorbitan trioleate | 13.5 |
| Trichlorofluoromethane | 910.0 |
| Dichlorodifluoromethane | 490.0 |

(i) Aerosol II — mg/ml

| | |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

(j) Aerosol III — mg/ml

| | |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

(k) Aerosol IV — mg/ml

| | |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

I claim:

1. A thiazole derivative of the formula I

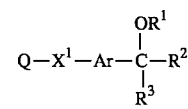

wherein Q is 2-oxo-1,2,3,4-tetrahydroquinolin-6-yl or 2-oxo-1,2-dihydroquinolin-6-yl which bears on the nitrogen atom at the 1-position a (1–4C)alkyl substituent;

$X^1$ is thio, sulphinyl or sulphonyl;

Ar is thiazolediyl;

$R^1$ is (1–4C)alkyl, (3–4C)alkenyl or (3–4C)alkynyl; and $R^2$ and $R^3$ together form a group of the formula —$A^2$—$X^2$—$A^3$— which together with the carbon atom to which $A^2$ and $A^3$ are attached define a ring having 5 or 6 ring atoms, wherein $A^2$ and $A^3$ which may be the same or different, each is (1–3C)alkylene and $X^2$ is oxy, and which ring may bear one or two (1–4C)alkyl substituents;

or a pharmaceutically-acceptable salt thereof.

2. A thiazole derivative of the formula I as claimed in claim 1 wherein Q is 2-oxo-1,2,3,4-tetrahydroquinolin-6-yl or 2-oxo-1,2-dihydroquinolin-6-yl which bears on the nitrogen atom at the 1-position a (1–4C)alkyl substituent;

$X^1$ is thio, sulphinyl or sulphonyl;

Ar is 2,5-thiazolediyl (with the $X^1$ group in the 2-position);

$R^1$ is (1–4C)alkyl, (3–4C)alkenyl or (3–4C)alkynyl; and $R^2$ $R^3$ and together form a group of the formula —$A^2$—$X^2$—$A^3$— which together with the carbon atom to which $A^2$ and $A^3$ are attached define a ring having 5 or 6 ring atoms, wherein $A^2$ and $A^3$ which may be the same or different, each is (1–3C)alkylene and $X^2$ is oxy, and which ring may bear one or two (1–4C)alkyl substituents;

or a pharmaceutically-acceptable salt thereof.

3. A thiazole derivative of the formula I as claimed in claim 1 wherein Q is 1-methyl-2-oxo-1,2,3,4-tetrahydroquinolin-6-yl;

$X^1$ is thio or sulphonyl;

Ar is 2,5-thiazolediyl (with the $X^1$ group in the 2-position);

$R^1$ is methyl; and $R^2$ and $R^3$ together form a group of the formula —$A^2$—$X^2$—$A^3$— which together with the carbon atom to which $A^2$ and $A^3$ are attached define a ring having 6 ring atoms, wherein each of $A^2$ and $A^3$ is ethylene and $X^2$ is oxy, and which ring may bear a methyl substituent alpha to $X^2$;

or a pharmaceutically-acceptable salt thereof.

4. A thiazole derivative of the formula I as claimed in claim 1 wherein Q is 1-methyl-2-oxo-1,2,3,4-tetrahydroquinolin-6-yl, $X^1$ is thio or sulphonyl;

Ar is 2,5-thiazolediyl (with the $X^1$ group in the 2-position);

$R^1$ is methyl; and $R^2$ and $R^3$ together form a group of the formula —$CH_2CH_2OCH(CH_3)CH_2$—;

or a pharmaceutically-acceptable salt thereof.

5. The thiazole derivative of the formula I as claimed in claim 1 being;

(2S,4R)-4-methoxy-2-methyl-4-[2-(1-methyl-2-oxo-1,2,3,4-tetrahydroquinolin- 6-ylthio)thiazol-5-yl]tetrahydropyran;

or a pharmaceutically-acceptable salt thereof.

6. A pharmaceutical composition which comprises a thiazole derivative of the formula I, or a pharmaceutically-acceptable salt thereof, as claimed in any one of claims 1 to 5, in association with a pharmaceutically-acceptable diluent or carrier.

7. A method of treating a disease or medical condition mediated alone or in part by one or more leukotrienes which comprises administering to a warm-blooded animal requiring such treatment an effective amount of a thiazole derivative of the formula I, or a pharmaceutically-acceptable salt thereof, as claimed in any one of claims 1 to 5.

* * * * *